United States Patent [19]

O'Donnell, Jr.

[11] Patent Number: 5,370,641

[45] Date of Patent: Dec. 6, 1994

[54] LASER TRABECULODISSECTION

[76] Inventor: Francis E. O'Donnell, Jr., 709 The Hamptons La., Town & Country, Mo. 63017

[21] Appl. No.: 886,926

[22] Filed: May 22, 1992

[51] Int. Cl.$^5$ .................. A61B 17/00; A61N 5/00
[52] U.S. Cl. ............................ 606/4; 606/5; 606/6; 606/166; 128/898
[58] Field of Search .............. 606/6, 5, 4, 166; 128/898

[56] References Cited

U.S. PATENT DOCUMENTS

| | | | |
|---|---|---|---|
| 4,558,698 | 12/1985 | O'Dell | 606/6 |
| 4,846,172 | 7/1989 | Berlin | 606/4 |
| 5,123,902 | 6/1992 | Müller et al. | 606/4 |
| 5,129,895 | 7/1992 | Vassiliadis et al. | 606/6 |

FOREIGN PATENT DOCUMENTS

| | | | |
|---|---|---|---|
| 1565484 | 5/1990 | U.S.S.R. | 606/6 |
| 1621920 | 1/1991 | U.S.S.R. | 606/6 |
| 1623646 | 1/1991 | U.S.S.R. | 606/6 |
| 1664311 | 7/1991 | U.S.S.R. | 606/6 |
| 9112046 | 8/1991 | WIPO | 606/6 |
| 9117793 | 11/1991 | WIPO | 606/6 |

*Primary Examiner*—Stephen C. Pellegrino
*Assistant Examiner*—Sonya C. Harris
*Attorney, Agent, or Firm*—Paul M. Denk

[57] ABSTRACT

This invention contemplates the use of a surgical laser device characterized by ultra-violet or infrared radiation to achieve controlled trabeculodissection in selected regions of the trabecular meshwork and Schlemm's Canal. The surgical laser is positioned over the corneoscleral bed for non-contact delivery, or, alternatively, it is inserted under a sclera flap with a contact tip and laser radiation is directed toward the trabecular meshwork and canal of Schlemm creating an ultra-thin trabecular meshwork and Canal of Schlemm. The outflow of aqueous humor through the disected trabecular meshwork functions as a self-limiting end point to the surgery when the aqueous humor absorbs the laser energy.

5 Claims, 4 Drawing Sheets

LASER TRABECULODISSECTION

BACKGROUND OF THE INVENTION

This invention relates generally to a method of controlling open-angle glaucoma by surgery and more specifically to the use of a laser in surgery to reduce the thickness of the trabecular meshwork and tissue around Schlemm's Canal to increase filtration of the aqueous humor and thereby controlling the open-angle glaucoma.

Primary open-angle glaucoma is a disease of unknown etiology known also as simple glaucoma, chronic glaucoma, glaucoma simplex, compensated glaucoma, and open angle glaucoma. The disease is characterized by the increase in intraocular pressure which results in atrophy of the optic nerve, visual field disturbances, and eventual blindness. In primary open-angle glaucoma the anterior-chamber angle appears normal to direct observation, and the aqueous humor has free access to the trabecular meshwork. Secondary open-angle glaucoma can occur because of fibrovascular proliferation and the trabecular meshwork is abnormal due to other eye diseases. Obstruction of the trabecular meshwork prevents the filtration of aqueous humor with a resulting increase in intraocular pressure.

Open angle glaucoma can be treated medically or surgically. The preferred treatment is medical and is directed toward increase in The outflow of aqueous humor from the anterior chamber of the eyeball or by decreasing the secretion of aqueous humor, or both.

Primary open-angle glaucoma is treated with drugs such a timolol, an adrenergic receptor antagonist; pilocarpine, a cholinergic stimulating drug; echothiophate iodide, a cholinesterace antagonist; epinephrine, an alpha and beta agonist; and acetazolamide, a carbonic anhydrase inhibitor.

There are problems inherent with medical treatment. Miotic drugs like pilocarpine may aggravate the visual loss caused by incipient cataract or may induce painful ciliary muscle spasm. Epinephrine may be irritating to the eye. Echothiophate iodide has a myriad of adverse effects, drug interactions, and contraindications, as does acetazolamide. Timolol is contraindicated in patients with asthma and other pulmonary diseases.

If the disease cannot be controlled by drugs and there is progress in the associated visual field defects and severity of optic nerve atrophy, surgery is indicated.

The main surgical procedure in open-angle glaucoma in which the trabecular meshwork is visible is laser trabeculoplasty, commonly using an argon laser. The eye is anesthetized and the trabecular meshwork is visualized through a gonioprism. The laser energy is applied ab externo, to photocoagulate the trabecular meshwork, often 50 to 100 spots, spaced evenly over the entire circumference of the anterior trabecular meshwork. The laser can reduce the circumference of the trabecular ring by heat induced shrinkage of the collagen of the sheet of trabecular tissue or by scar tissue contraction at the burn sites, forcing the ring to move toward the center of the anterior chamber, elevating the sheets, and pulling open the intertrabecular spaces. Flow is increased through the trabecular spaces. The main complication in this type of surgery is a transient increase in intraocular pressure that may require medication to control. Control is usually achieved in about 85% of all patients, but most (75%) continue to require medicines. However, control can be lost with the passing of time and additional laser trabeculoplasty may not be effective.

In eyes where laser trabeculoplasty cannot be performed or where it fails to control pressure, a filtering operation is indicated. All previous filtering operations were based on the theory of creating a fistula between the anterior chamber and the sub-conjuctival space through which aqueous humor can flow. Generally, the surgery was performed by scalpel. Trabeculectomy is the operation of choice. An operating microscope is used and a scleral flap is fashioned to expose the trabecular meshwork. A portion of the meshwork is exised and the scleral flap is replaced. A filtering bleb often develops after surgery. This surgery is performed in an operating surgery suite, and complications can include excessively low intraocular pressure, flat anterior chamber, endophthalmitis, cataract, sympathetic ophthalmic and bullous keratopathy. Furthermore, a mechanical disection has limited success because of the difficulty in judging the depth of dissection of the trabecular meshwork and the surgeon can inadvertently enter the anterior chamber with his surgical tool.

SUMMARY OF THE INVENTION

A principle object of the current invention is to provide a method for surgically treating open-angle glaucoma wherein the surgery is performed using laser surgical device to perform a trabeculodissection.

Another object of this invention is to provide a method of performing trabeculodissection that includes a self-limiting end point in surgery when the laser energy is absorbed by the flowing aqueous humor.

Yet another object of the invention is to provide a method to remove the tissue from the trabecular meshwork leaving a smooth and even treatment surface.

Still another object of the invention is to provide a method for trabeculodissection that avoids entry into the anterior chamber of the eyeball.

Yet another object of this invention is to provide a method of trabeculodissection that avoids entry into the eye, lowers the risk of complications, can be done in the surgeon's office under local anaesthesia, thereby enhancing patient convenience and comfort and reducing the associated health care cost.

These and other objects will become more apparent to those skilled in the art upon reviewing the summary of this invention in addition to undertaking a study of the preferred embodiment.

In accordance with these objectives, there is provided a method for surgically treating open-angle glaucoma using laser surgery on the corneoscleral bed under a scleral flap, tissue is removed until sufficient aqueous humor is coming through the ultra-thin remaining Schlemm's Canal and trabecular meshwork. The energy of the laser is absorbed by the outflowing aqueous humor thereby creating a self-regulating end point. The scleral flap is replaced with or without a suture. There is no entry into the eyeball itself and complications are thereby reduced.

DESCRIPTION OF THE PREFERRED EMBODIMENT

The present invention discloses a method for surgically treating glaucoma.

Figure 1:
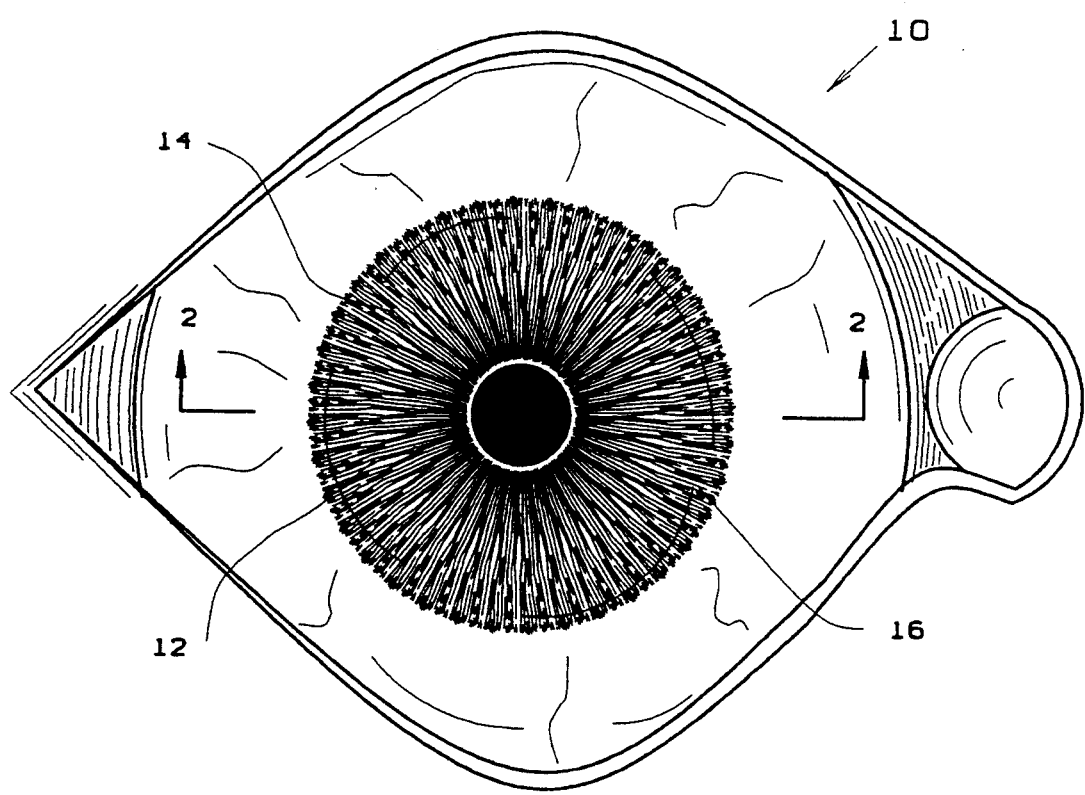
FIG. 1 is a front elevational view of the human eyeball.

FIG. 1 is a front elevational view of the human eye shown generally at 10 and illustrating several structures relevant to the present invention including iris 12, pupil 14, and limbus 16.

Figure 2:
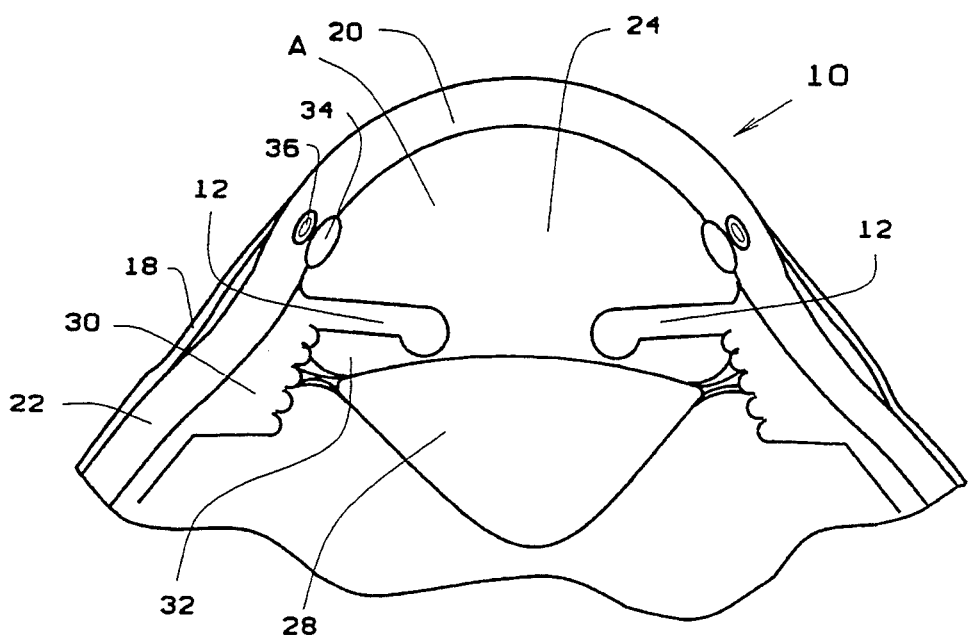
FIG. 2 is a fragmentary cross-sectional view of the eyeball as viewed across lines 2—2 of FIG. 1.

FIG. 2 illustrates a fragmentary cross-sectional view of the human eye. The eye is covered by conjunctiva 18, a mucous membrane. An outer, fibrous tunic consists of cornea 20 anteriorly and sclera 22, posteriorly. Cornea 20 is a transparent part of the external tunic, almost circular in outline, convex anterioraly, and projects like a dome above scelra 22. Sclera 22 is a tough, elastic membrane which maintains the size and shape of the eyeball. Anterior chamber 24 is formed between cornea 20 and iris 12. Lens 28 is posterior to iris 12 and suspended between ciliary body 30. Anterior chamber 24 is filled with aqueous humor A, a watery transparent liquid containing traces of albumin and salts produced by iris 12, ciliary body 30 and cornea 20. Generally, the aqueous humor circulates through anterior chamber 24 and posterior chamber 32. One route of drainage of the aqueous humor is filtration through trabecular meshwork 34 into Canal of Schlemm 36 and into the surrounding vasculature (not shown).

Figure 3A:
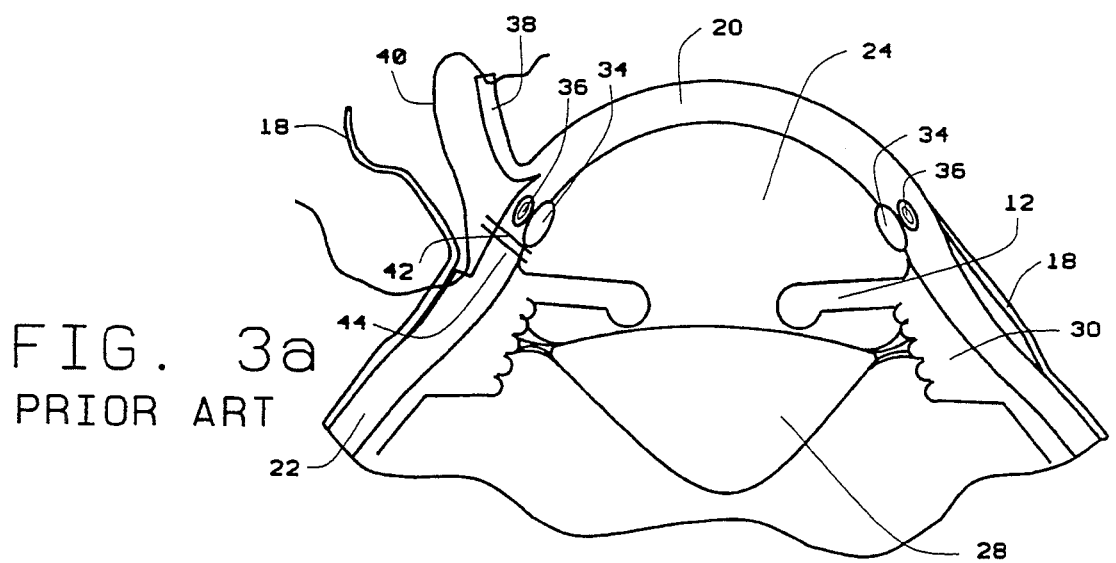
FIG. 3a is a fragmentary cross-sectional view similar to FIG. 2 illustrating a step in a prior art technique.
Figure 3B:
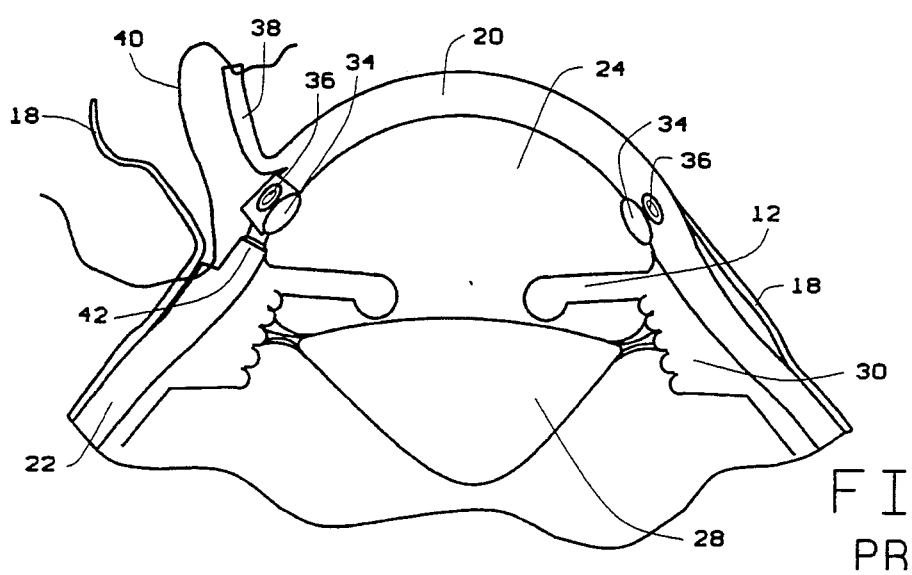
FIG. 3b is another fragmentary cross-sectional view similar to FIG. 2 illustrating another step in a prior art technique.
Figure 3C:
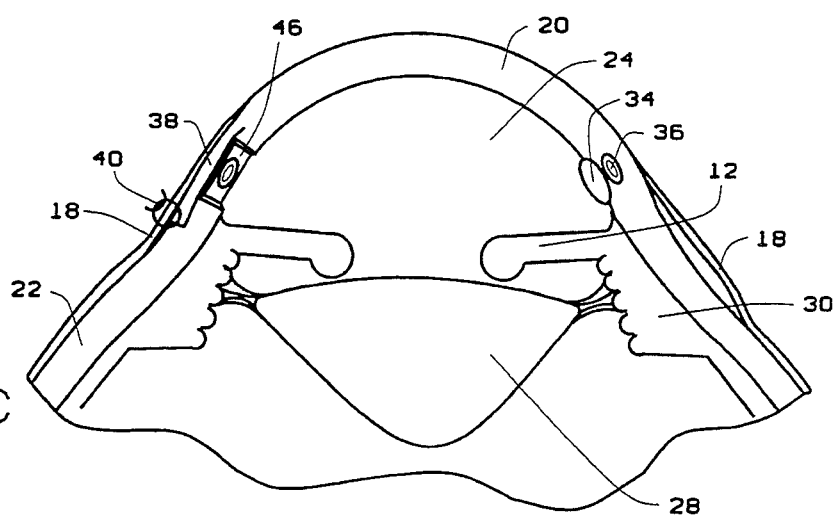
FIG. 3c is another fragmentary cross-sectional view similar to FIG. 2 illustrating yet another step in a prior art technique.

Glaucoma, a disease of the eye characterized by increased intraocular pressure, can be relived by enhancing filtration of aqueous through trabecular meshwork 34 into Schlemm's Canal 36. FIGS. 3a-3c illustrate a common prior art technique for enhancing aqueous outflow through trabecular meshwork 34 and Schlemm's Canal 36. The surgeon makes an incision with a scalpel through conjunctiva 18 and flap 38 is cut from scelra 22 near limbus 16. Preplaced suture 40 is placed to close the incision when the procedure is finished. Incision 42 (approximately 4 mm) is made along the line of scleral spur 44 to anterior chamber 24. At this point, the scalpel can inadvertently enter deeply into anterior chamber 24 increasing complications and allowing outflow of aqueous humor causing anterior chamber 24 to collapse. Mechanical dissection has met with limited success because of the difficulty of judging what disection depth will be adequate to increase flow without inadvertently entering anterior chamber 24.

The anterior lip of incision 42 is grasped with a pair of iris forceps (not shown) and excised removing a length of Canal of Schlemm 36 and trabecular meshwork 34 (see particularly FIGS. 3b and 3c). Flap 38 is secured back in place with suture 40 or by laser welding. The opened area, generally shown at 46 (FIG. 3C), allows enhanced outflow of aqueous humor and decrease of intraocular pressure.

Figure 4:
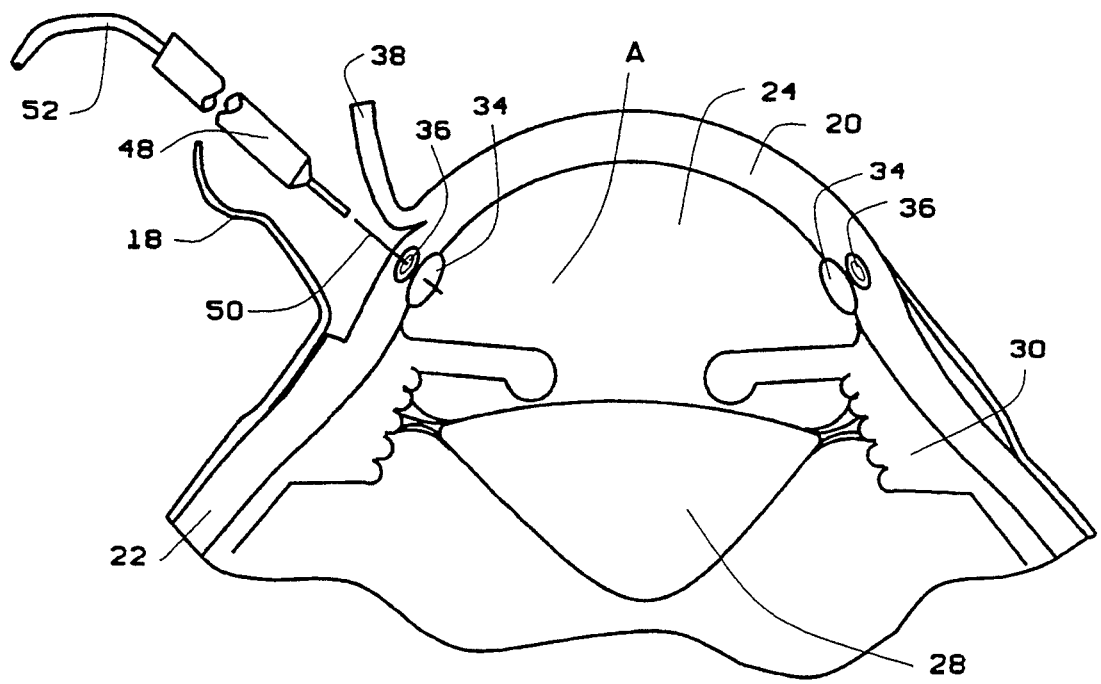
FIG. 4 is a fragmentary cross-sectional view similar to FIG. 2 illustrating a step in the technique of the present invention.
Figure 5:
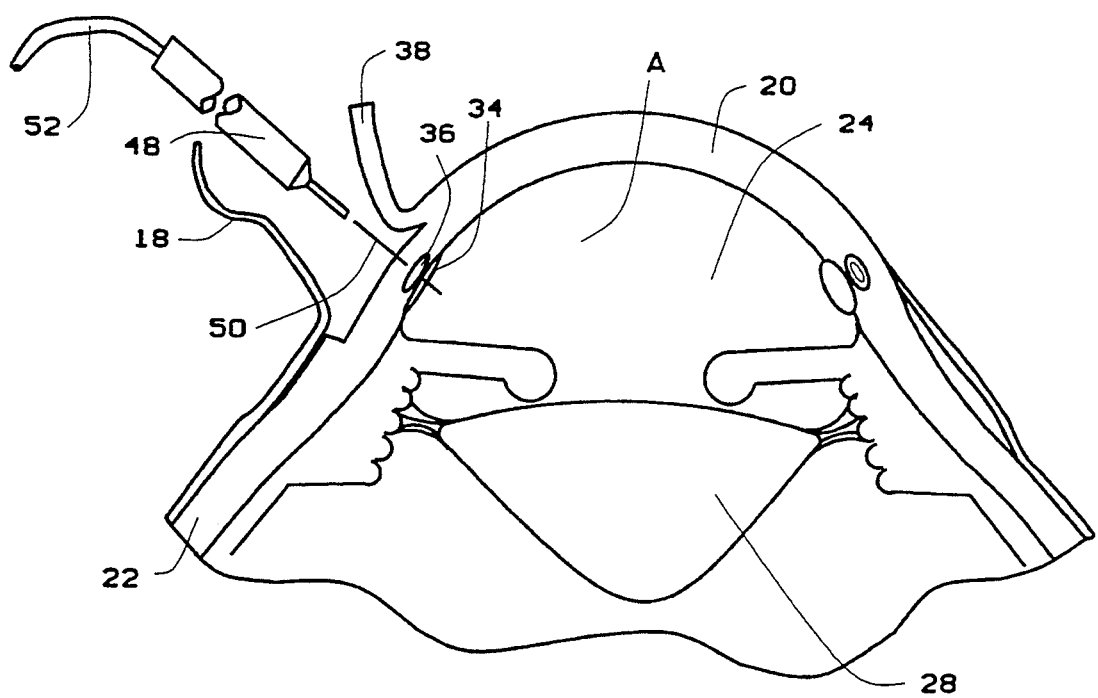
FIG. 5 is another fragmentary cross-sectional view, similar to FIG. 4, illustrating another step in the technique of the present invention.
Figure 6:
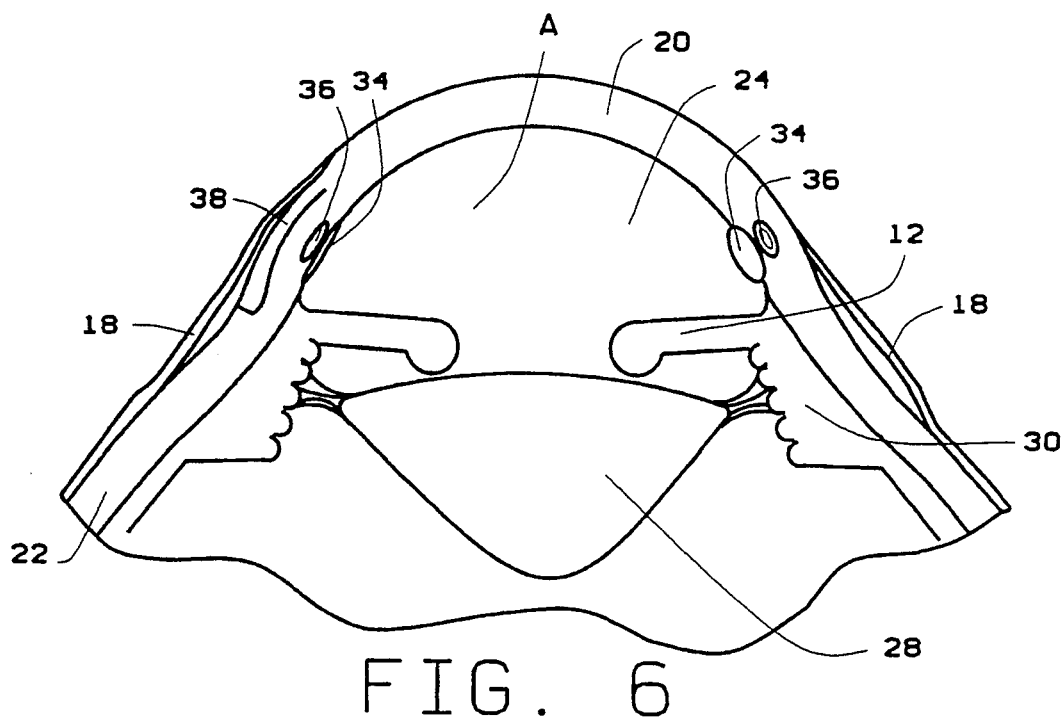
FIG. 6 is another fragmentary cross-sectional view, similar to FIG. 5, illustrating another step in the technique of the present invention.

FIGS. 4-6 disclose the technique of the present invention. Scleral flap 38 is created by conventional surgical procedure using a scalpel. In an alternative embodiment of the procedure (not shown) flap 38 is formed using a laser cutting technique.

Laser 48 is inserted under flap 38, or flap 38 is retracted. Laser 48 is positioned to bring the laser beam to bear on the corneascleral bed, or alternatively, the laser handpiece is connected by fiberoptic cable 52 to a laser energy source (not shown) emitting, for example, ultraviolet energy, or perhaps the Erbium laser may transmit other effective wave-lengths. The ultraviolet emitting laser may be a VISIX 20/20 excimer laser. Energy 50 is directed to the area under flap 38 including trabecular meshwork 34 and Canal of Schlemm 36. Aqueous humor A flowing from chamber 24 will absorb energy 50 and serve as a self-regulating end-point to the procedure to prevent cutting too deeply through anterior chamber 24. The surgeon removes the outer part of Canal of Schlemm 36 and trabecular meshwork 34 in small fractions of micron sizes leaving a smooth, even treatment surface. Energy 50 is directed to the area of Canal of Schlemm 36 and trabecular meshwork 34 until the surgeon determines that sufficient aqueous humor is coming through the remaining ultra-thin Schlemm's Canal 36 and trabecular meshwork 34.

As illustrated by FIG. 6, laser 48 is withdrawn and flap 38 is replaced. A suture (not shown) can be placed to secure the flap if necessary and conjunctiva 18 is replaced.

Figure 7:
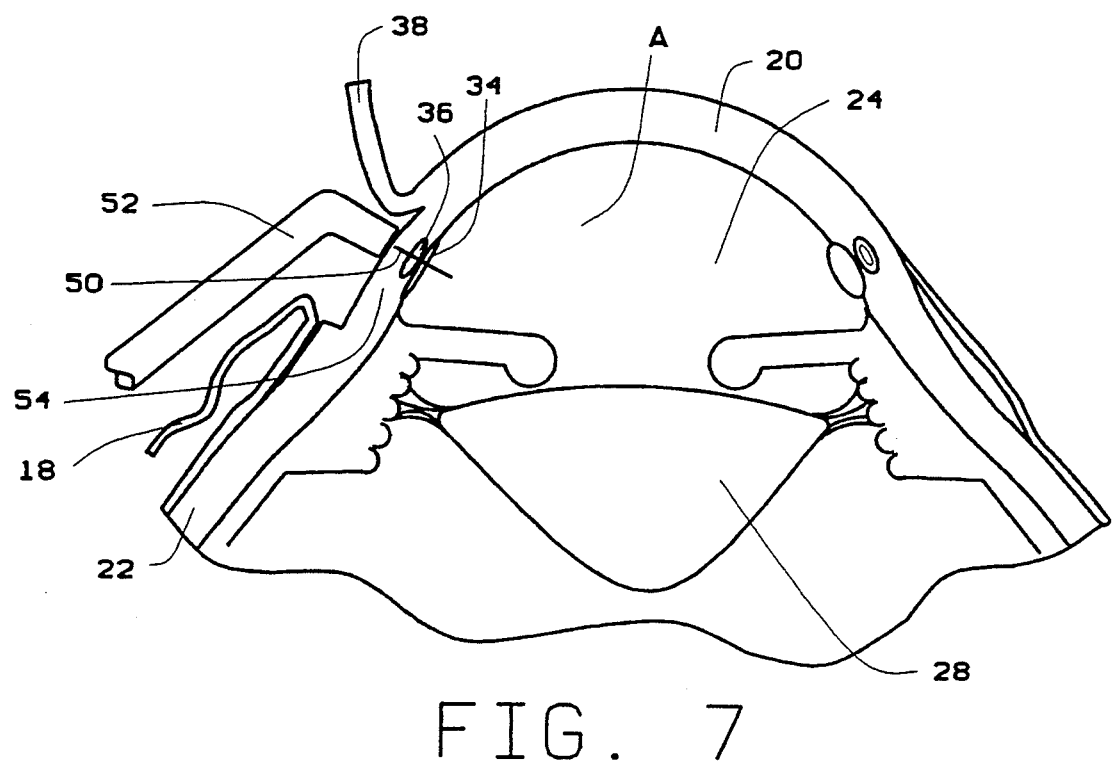
FIG. 7 is another cross-sectional view, similar to FIG. 5, illustrating an alternative embodiment of the technique of the present invention.

In another embodiment of the invention, FIG. 7, the surgeon uses a contact laser probe handpiece 52 and inserts it under scleral flap 38 and it is placed in contact with the corneascleral tissue 54. The laser is activated and energy transmitted to the meshwork 34 and the Canal of Schlemm 36.

In view of the above, it will be seen that the various objects and features of the present invention are achieved and other advantageous results obtained.

As various changes could be made in the above process without departing from the scope of the invention, it is intended that all matter contained in the above description and shown in the accompanying drawings shall be interpreted as illustrative and not in a limiting sense.

Having thus described the invention, what is claimed and desired to be secured by Letters Patent is:

1. A method for performing a non-penetrating trabeculectomy on the sclera and conjunctiva at the corneasclera bed for treating glaucoma which has formed blockage in the passage of aqueous humor from the anterior chamber and through the trabecular meshwork and the Schlemm's Canal, comprising:
   (a) cutting a flap in the sclera;
   (b) positioning a laser surgical instrument under the scleral flap;
   (c) utilizing laser energy to remove tissue in micron sizes from the trabecular meshwork and to form a substantially small passage through the Schlemm's Canal, and thereby creating a smooth and even treatment surface thereat, thereby enhancing the outflow of fluid through the trabecular meshwork and through the Schlemm's Canal;

(d) withdrawing the laser surgical instrument from under the formed scleral flap;
(e) replacing the scleral flap; and
(f) replacing and fixing the scleral flap in place through one of suture and laser welding.

2. The method of claim 1 wherein the cutting of the scleral flap further comprising the cutting through the conjunction and sclera with a scalpel.

3. The method of claim 1 wherein the removal of tissue from the corneasclera bed is performed with the laser in micron steps leaving a smooth and even treatment surface upon the trabecular meshwork and the Schlemm's Canal.

4. The method of claim 1 wherein the creating of the scleral flap further comprises cutting through the conjunctiva with a scalpel and then cutting through the sclera with a surgical scissors.

5. The method of claim 1 wherein the inserting of the laser through the scleral flap further comprising inserting one of an ultraviolet and infrared energy emitting laser.

* * * * *

UNITED STATES PATENT AND TRADEMARK OFFICE
CERTIFICATE OF CORRECTION

PATENT NO. : 5,370,641

DATED : December 6, 1994

INVENTOR(S) : Francis E. O'Donnell, Jr.

It is certified that error appears in the above-identified patent and that said Letters Patent is hereby corrected as shown below:

```
    Column 5, line 8, change "conjunction" to
---conjunctiva---.
```

Signed and Sealed this

Twenty-first Day of February, 1995

*Attest:*

BRUCE LEHMAN

*Attesting Officer*     *Commissioner of Patents and Trademarks*